United States Patent [19]

Blumbergs

[11] Patent Number: 5,296,589
[45] Date of Patent: Mar. 22, 1994

[54] HYDROGENATION OF 2-FLUORO-9-(2,3,5-TRI-O-BENZYL-BETA-D-ARABINOFURANOSYL)ADENINE

[75] Inventor: Peter Blumbergs, Royal Oak, Mich.

[73] Assignee: Ash Stevens, Inc., Detroit, Mich.

[21] Appl. No.: 876,412

[22] Filed: Apr. 30, 1992

Related U.S. Application Data

[63] Continuation-in-part of Ser. No. 445,446, Dec. 4, 1989, Pat. No. 5,110,919.

[51] Int. Cl.$^5$ .................. C07H 19/167; A61K 31/70
[52] U.S. Cl. .................................... 536/27.7; 536/55.3
[58] Field of Search ................ 536/24, 26, 55.3, 27.7

[56] References Cited

U.S. PATENT DOCUMENTS

| | | | |
|---|---|---|---|
| Re. 29,835 | 11/1978 | Witkowski et al. | 536/29 |
| 4,188,378 | 2/1980 | Montgomery | 514/46 |
| 5,110,919 | 5/1992 | Blumbergs et al. | 536/24 |

OTHER PUBLICATIONS

Keller, F., et al., J. Org. Chem. 32, 1644–1646 (1967).
Imai et al., J. Org. Chem. 42: 2309–2313, 1977.
Montgomery et al., in J. Hetero. Chem. 16, 157 (1979).

*Primary Examiner*—Johnnie R. Brown
*Assistant Examiner*—Gary L. Kunz
*Attorney, Agent, or Firm*—Ian C. McLeod

[57] ABSTRACT

A process for the preparation of 2-fluoro-9-beta-D-arabinofuranosyl purine (VII) by a reaction of palladium chloride and hydrochloric acid with 2-fluoro-9-(2,3,5-tribenzyl-beta-D-arabinofuranosyl)adenine (VI) at elevated pressures in a solvent for (VI) is described. The reaction is rapid, economical and efficient.

6 Claims, No Drawings

HYDROGENATION OF 2-FLUORO-9-(2,3,5-TRI-O-BENZYL-BETA-D-ARABINOFURANOSYL)ADENINE

CROSS-REFERENCE TO RELATED APPLICATION

This application is a continuation-in-part of application Ser. No. 445,446, filed Dec. 4, 1989, now U.S. Pat. No. 5,118,919.

BACKGROUND OF THE INVENTION

(1) Field of the Invention

The present invention relates to a process for the preparation of 2-fluoro-9-beta-D-arabinofuranosyl adenine (VII) which is useful in the preparation of 2-Fluoro-Ara-AMP (the phosphate of (III), a cytotoxic agent. The compound (VII) is also known as 9-beta-D-arabinofuranosyl-2-fluoroadenine or 2-F-Ara-A.

(2) Prior Art

Example 4A of U.S. Pat. No. 4,188,378 to Montgomery shows the preparation of 2-fluoro-9-beta-D-arabinofuranosyl adenine (VII) from 2-fluoro-9-(2,3,5-tribenzyl-beta-D-arabinofuranosyl)adenine )VI) using sodium in liquid ammonia with a 34% yield. The most efficient procedure disclosed in this patent is the use of boron trichloride in methylene chloride in Example 4B which produces a 91% yield, but which is difficult and expensive to perform on a large scale since the reaction is performed at −80° C. using liquid nitrogen or dry ice acetone. The reference describes catalytic hydrogenolysis of (VI) in the presence of palladium or palladized charcoal to remove the benzyl group. It suggests that partial defluorination results from this reaction.

J. Org. Chem. 1977, 42, 2309, describes hydrogen transfer from an organic compound to chlorobenzene. Under the reaction conditions employed, fluorobenzene did not react.

OBJECTS

It is therefore an object of the present invention to provide an improved process for the preparation of 2-fluoro-9-beta-D-arabinofuranosyl adenine (VII) in high yield. Further still, it is an object of the present invention to provide a process which is rapid and economical on a commercial scale. These and other objects will become increasingly apparent by reference to the following description.

GENERAL DESCRIPTION

The present invention relates to a process for the preparation of 9-beta-D-arabinofuranosyl-2-fluoroadenine (VII) which comprises reacting a reaction mixture of 2-fluoro-9-(2,3,5-tri-o-benzyl-beta-D-arabinofuranosyl)adenine (VI) dissolved in a non-reactive solvent for (VI) with hydrogen and a molar amount of palladium chloride less than (VI) and concentrated hydrochloric acid in a molar excess to (VI) in a sealed vessel at an elevated pressure above atmospheric pressure to produce (VII) in the reaction mixture; removing the palladium chloride from the reaction mixture; neutralizing the reaction mixture; and separating (VII) from the reaction mixture.

The solvents used in the reaction mixture dissolve (VI). Preferably these are ethanol, methanol, ethoxyethanol, or methoxyethanol, which is most preferred.

The pressure is preferably between about 30 and 50 psig. The most preferred pressure is 35 psig.

Generally the reaction mixture is started at ambient temperatures or less, preferably about 17° C. The temperature goes to about 38° to 40° C. during the reaction. No attempt is made to control the reaction temperature.

SPECIFIC DESCRIPTION

An eight-step sequence for the preparation of 2-Fluoro-Ara-AMP including compounds (VI) and (VII) was as follows:

Reaction Sequence
2-Fluoro-Ara-AMP (Fludarabine Phosphate)

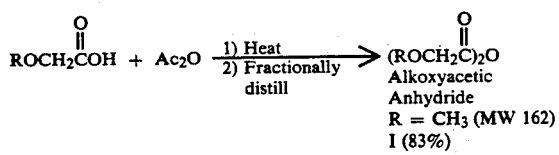

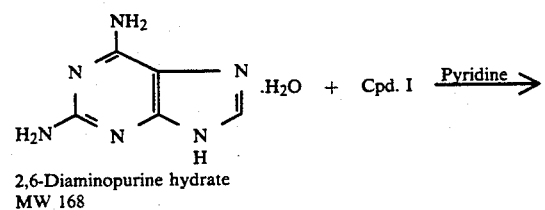

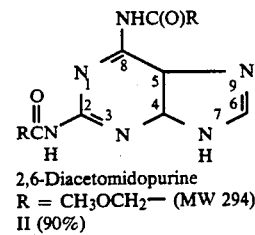

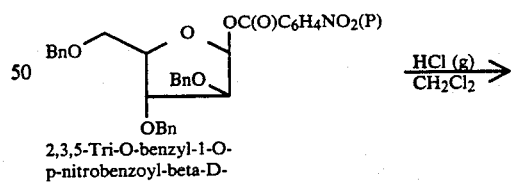

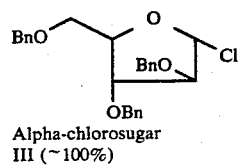

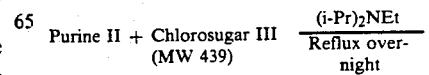

-continued
Reaction Sequence
2-Fluoro-Ara-AMP (Fludarabine Phosphate)

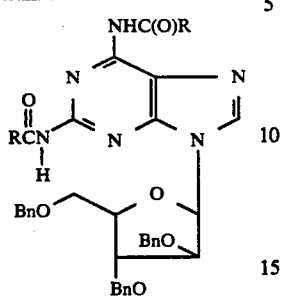

R = CH₃OCH₂— (MW 697)
IV (101%)

Compound IV (MW 697) →(2) NaOCH₃—CH₃OH)→

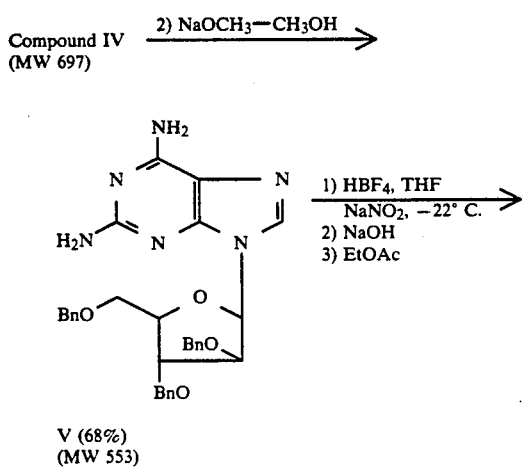

V (68%) (MW 553)

1) HBF₄, THF / NaNO₂, −22° C.
2) NaOH
3) EtOAc

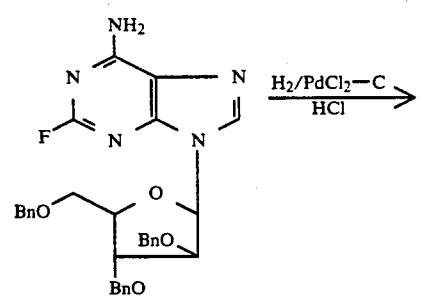

VI (39%) (MW 556)

H₂/PdCl₂—C / HCl →

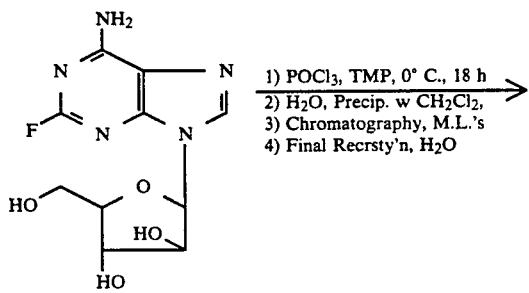

VII (80%) (MW 285.4)

1) POCl₃, TMP, 0° C., 18 h
2) H₂O, Precip. w CH₂Cl₂,
3) Chromatography, M.L.'s
4) Final Recrsty'n, H₂O -continued
Reaction Sequence
2-Fluoro-Ara-AMP (Fludarabine Phosphate)

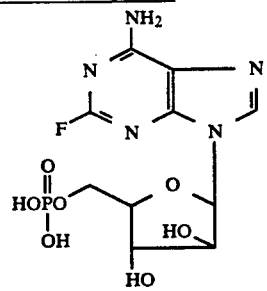

VIII (56%) (MW 365.2)
2-Fluoro-ara-AMP
(Fludarabine Phosphate)

Application Ser. No. 445,446, filed Dec. 4, 1989 describes the process steps in detail. The present invention is concerned with the conversion of VI to VII. Previous reports (Montgomery, U.S. Patent and J. Het. Chem previously cited) state that catalytic hydrogenation results in partial defluorination. The procedure described herein where the hydrogenation is conducted in the presence of hydrochloric acid avoids defluorination and simplifies the purification procedure.

EXPERIMENTAL

Example 1

Methoxyacetic anhydride (I)

A mixture of methoxyacetic acid (360 g, 4 mol) and acetic anhydride (409 g, 4 mol) was heated with stirring in a 2 L 3-neck flask equipped with a bubble-plate distillation column and a fraction cutter. A mixture of acetic acid and acetic acid anhydride was distilled at atmospheric pressure until the internal temperature reached 164° C. The pressure was reduced and the product was collected at 65°–71° C. at 0.2 mmHg to give 229 g (71%) of pure title compound. A total of 34.8 kg of methoxyacetic acid was processed to give 26.1 kg (83%) of the anhydride (I).

Materials

Methoxyacetic acid
Acetic anhydride

2,6-Di(methoxyacetamido)purine (II)

A mixture 2,6-diaminopurine monohydrate (504 g, 3.0 mol) and methoxyacetic anhydride (1.53 kg, 9.46 mol) in pyridine (3.5 L) was heated (steam bath) with stirring. The temperature rose to 88° C. in about 10 minutes and the mixture became homogeneous; then the temperature rose spontaneously to 103° C. (exotherm). The reaction mixture was stirred for one hour during which time the temperature dropped to 97° C. and solid started to precipitate. Heating was discontinued and the reaction temperature fell to 58° C. The mixture was gradually diluted with methyl ethyl ketone (3.5 L) and then stirred slowly overnight. the solid was collected and the filter cake was washed with methyl ethyl ketone (800 mL). The cake was transferred to a beaker and stirred with methyl ethyl ketone (6 L). The solid product was collected by filtration, washed with methyl ethyl ketone (2 L) and air-dried overnight. The air-dried material was then dried to constant weight at 80°–85° C./0.3 mmHg for 18 hours to give 790 g (90%) of the title diamide (II), mp 219°–220° C.

In this manner a total of 7.35 kg of 2,6-diaminopurine and 22.33 kg of methoxyacetic anhydride (I) were processed to yield 11.70 kg (91%) of the title diamide II.

Anal. Calcd. for $C_{11}H_{14}N_6O_4$(294.27): C, 44.89; H, 4.79; N, 28.56. Found: C, 44.91; H, 4.71; N, 28.36.

Materials 2,6-Diaminopurine
Methyl ethyl ketone
Methoxyacetic anhydride
Pyridine 2,3-5-Tri-O-benzyl-alpha-D-arabinosyl chloride (III)

Hydrogen chloride gas was bubbled into a mechanically-stirred solution of 2,3,5-tri-O-benzyl-1-O-p-nitrobenzoyl-beta-D-arabinofuranose (1.25 kg, 2.2 mol) in methylene chloride (6.25 L) at 4°–6° C. for two hours. The reaction mixture was warmed to 16° C., and the mixture purged with $N_2$ for 10 minutes and filtered through a sintered glass dispersion tube. The residual solid p-nitrobenzoic acid was washed with methylene chloride (2×1.25 L). The solvent was removed (aspirator) with stirring at 23°–27° C. (internal) until most of the methylene chloride was removed. Ethylene dichloride (EDC, 1.25 L) was added and then removed (aspirator) to an internal temperature of 37° C.

Titration of the liberated p-nitrobenzoic acid indicated that the yield of the chloro sugar III was essentially quantitative in agreement with the weight of the syrup, 975 g 101%.

Materials 2,3,5-Tri-O-benzyl-1-O-p-nitrobenzoyl
beta-D-arabinose
Methylene chloride
Hydrogen chloride, gas
Ethylene dichloride 2,6-Di(methoxyacetamido)-9-(2,3,5-tri-O-benzyl-beta-D-arabinofuranosyl)purine (IV)

2,6-Di(methoxyacetamido)purine (II) (646 g, 2.20 mol) was suspended in ethylene dichloride (EDC) (4.8 L). The mixture was dried by removing 600 mL of the EDC by distillation. The concentrated solution of the above-prepared alpha-chloro sugar III (2.20 mol) was added to the suspension, followed by freshly-distilled diisopropylethylamine (354 g, 2.75 mol). The mixture was refluxed overnight (steam bath) with stirring and the hot solution was poured into deionized water (4 L) with stirring. The organic phase was separated and the aqueous phase was washed with EDC (1.5 L). The combined organic phase was washed with deionized water (2×2 L). EDC was removed (aspirator, steam bath) with stirring. The residue was azeotroped with n-propanol (2 L) which was removed by distillation to give compound IV as a syrup. The yield was 1.55 kg, 101%, essentially quantitative.

Materials 2,6-Di(methoxyacetamido)purine (II)
Alpha-chlorosugar (III)
Ethylene dichloride
Diisopropylethylamine
n-Propanol 2-Amino-9-(2,3,5-tri-O-benzyl-beta-D-arabinofuranosyl)adenine (V)

The protected 2,6-di(methoxyacetamido)purine (IV) (1.55 kg, 2.20 mol) was dissolved in methanol (3.6 L) with stirring and warmed to 46°–48° C. A solution of sodium methoxide (30 g, 95%, 0.55 mol, in 250 mL methanol) was added and the solution was warmed to 61° C. The reaction was completed in about 1 hour (tlc) at which time the product started to precipitate. The mixture was allowed to cool to 30° C. and then refrigerated overnight. The product was collected, washed with ice-cold methanol (800 mL) and air-dried to give the title compound (V) 823 g (68%), mp 60°–62° C.

Materials

Intermediate (IV)
Sodium methoxide (95%)
Methanol, abs. (R)
Ether, anhydrous (R)

9-(2,3,5-Tri-O-benzyl-beta-D-arabinofuranosyl)-2-fluoroadenine (VI)

A mechanically-stirred suspension of the protected nucleoside (V) (300 g, 0.543 mol) in tetrahydrofuran (1.125 L) was cooled to −32° C. (dry ice-acetone). Fluoroboric acid (48%, 150 mL) was added over a period of 35–40 minutes. The temperature rose during the addition to −23° C. to −21° C. where it was maintained by cooling. A solution of sodium nitrite (62 g, 0.899 mol) in water (75 mL) was added over a period of 10 minutes, followed by the remaining fluoroboric acid (1 L) over a period of 55 minutes while maintaining the temperature between −23° C. to −21° C. throughout. The mixture was stirred for 2.5 hours at −23° C. to −21° C., then poured with stirring into a mixture of ethyl acetate (1.5 L) and ice (1.5 kg). A 50% solution of sodium hydroxide (510 mL) in water was added to adjust the pH to 8. The ethyl acetate phase was separated and the aqueous phase was extracted with ethyl acetate (1 L, 600 mL). The ethyl acetate phase and extract were combined, washed with deionized water (2×500 mL) and concentrated (aspirator, steam bath). The residue was azeotroped with benzene (2×750 mL) and the semisolid mass was dissolved in ethanol (360 mL). Benzene (70 mL) was added to the solution which was stirred and allowed to cool to 43° C. when solid material began to precipitate. At this point cold ethanol saturated with ammonia (360 mL) was added and the mixture was cooled rapidly to 24° C. (ice-bath). The mixture was then stored in the refrigerator overnight. The precipitate was collected, washed with ethanol (250 mL) and with petroleum ether (400 mL) and air-dried to give 129 g of crude product, mp 155°–7° C., containing organic by-products and residual salts.

In this manner, 3.10 kg of starting material (V) was processed to give 1.25 kg (40.1%) of crude product (VI). This was recrystallized as described below (Method A) to yield 1.00 kg (32.1%) of purified product, mp 156.5°–158° C. and a second crop, 80 g (2.6%). Also, in the same manner, 240 kg of precursor V was processed to give 1.02 kg (42.3%) of crude VI. A second crop, 100 g, was isolated from the mother liquors. The 1.02 kg of crude (VI) was combined with the above 80 g second crop and recrystallized (Method B) to give 910 g of purified product and 97 g of a second crop. Thus, a total of 5.50 kg of precursor (V) was processed to give 1.91 kg (34.5%) of pure material used in the next step plus 207 g (3.7%) of second crop material.

Purification Procedures for Compound (VI)

Method A: The crude product (1.25 kg) was dissolved in 90% ethanol-benzene (10 mL/g; preheated to reflux) in two batches, 900 g and 350 g. Norit A (87.5 g) was added to the hot solution which was filtered through a celite pad using a steam-jacketed funnel. The filter cake was washed with 90% ethanol-benzene (1 L). The combined filtrate was allowed to cool to room temperature overnight. The solids were collected, washed with ethanol (1 L) and with petroleum ether (1.5 L) and dried at 60° C. at 0.3 mmHg for 2 hours to give 1.00 kg of purified product, mp 156°–58° C. The mother liquor was concentrated to 1.8 L (aspirator, steam bath). The precipitated solids were dissolved by heating the mixture to reflux. The solution was allowed to cool to room temperature. The resulting mixture was filtered to give 80 g of second crop material.

Method B: The procedure was the same as above except that the recrystallization solvent was 92% ethanol-toluene (10 mL/g) instead of 90% ethanol-benzene (10 mL/g).

Materials

2-Amino-9 (2,3,5-tri-O-benzyl-beat-D-arabinofuranosyl) adenine (V)
THF
Fluoroboric acid (48%)
Sodium nitrite
Ethyl acetate
Sodium hydroxide, 50% aq.
Ethanol, 3A, specially denatured
Ammonia, gas
Benzene
Toluene
Petroleum ether (35°–60° C.)
Norit A TM, acid-washed charcoal
Celite, analytical grade 9-beta-D-Arabinofuranosyl-2-fluoroadenine (VII)

Concentrated hydrochloric acid (0.5 mL/g of nucleoside, 50 mL, 0.608 mol) was added to a suspension of intermediate (VI) (100 g, 0.180 mol) in methoxyethanol (500 mL) to give a homogeneous yellow solution to which palladium chloride (3.0 g) and Norit A TM (10 g) were added. The temperature was about 17° C. to start and ended at about 38° C. to 40° C. The mixture was flushed with hydrogen (2×20 psig) and the hydrogen pressure was raised to 50 psig. After 10 minutes the pressure which had fallen to 2 psig was adjusted back to 50 psig. The process was repeated twice more until there was no further hydrogen uptake (total time, 50 minutes). No starting material was present by tlc. The catalyst was removed through a celite bed and the filter cake was washed with methoxyethanol (2×50 mL). The filtrate was cooled (ice-bath) and concentrated ammonium hydroxide (~55 mL) was added to pH ~8 (light-pink color). The precipitate (NH$_4$Cl) was removed by filtration and the filtrate was concentrated to near dryness. The resulting solid was slurried with water (150 mL), filtered and washed with ethanol (50 mL) to give 55 g of crude produce (air-dried). The crude product was recrystallized from hot ethanol-water (1.6 L, 1:1 v/v) to afford, after air-drying, 44 g (81% as a monohydrate) of the title nucleoside VII, mp 264°–266° C. (dec).

In this manner a total of 3.15 kg of protected nucleoside was processed to give 1.53 kg of crude air-dried product. The crude product was recrystallized from hot ethanol-water (30 mL/g, 46 L, 1:1 v/v) and dried at 90° C., 0.3 mmHg for 24 hours to give pure anhydrous title compound (VII), 1.295 kg (80%, average yield), mp 264°–266° C. (dec); lambda max (H$_2$O) 261 nm ($\epsilon$=15,100).

Anal. Calcd for C$_{10}$H$_{12}$FN$_5$O$_4$ (285.24): C, 42.11; H, 2.42; F, 6.66; N, 24.55. Found: C, 42.00; H, 4.40; F, 6.60; N, 24.61.

Materials

2-Methoxyethanol
Palladium chloride
Concd. hydrochloric acid (37.3%)
Norit A
concd. ammonium hydroxide
Ethanol, 3A, specially denatured
Cellulose powder, CF-11

9-beta-D-arabinofuranosyl-2-fluoroadenine 5'-phosphate (VIII) NSC 312887

A typical 100 g run used to process the final 785 g of intermediate (VII) is described. Phosphorous oxychloride (80.0 g, 49 mL, 523 mmol) was added to cold (0° C., ice-bath) trimethylphosphate (1 L) and the solution was kept at 0° C. for 1 hour. 9-beta-D-Arabinofuranosyl-2-fluoroadenine (VII) (100.0 g, 350.6 mmol) was added with stirring in one portion. The reaction mixture became homogeneous (light-yellow solution) after two hours and 50 minutes. The reaction mixture was then placed in a refrigerator (−1° C.) for 15 hours. No starting material was present by tlc. Water (70 mL) was added and the solution was stirred for 3 hours at 0° C. The mixture was then poured into cold (−0° C., ice-bath) methylene chloride (8 L) with stirring and held in the ice-bath with stirring until a clear methylene chloride phase was obtained (1 h). The methylene chloride was removed by decantation and the residual yellowish, gummy mass was dissolved in warm (~50° C.) water (700 mL). The solution was seeded and allowed to stand at room temperature overnight. The resulting crystalline product was collected by filtration and washed with water (50 mL) and with ethanol (2×50 mL). The product was dried at room temperature at 0.3 mmHg for 4 hours to give 78.5 g (tlc, trace impurities) of first crop material, mp 200°–205° C. (dec), with prior browning at ~185° C.

The methylene chloride supernatant liquid, which remained after the isolation of the crude gummy product, was extracted with water (3×500 mL). The water extracts were combined and percolated into a column containing Dowex-50 (acid form) resin (560×80 mm). The column was eluted with water and the fractions containing product (by UV monitor and tlc) were combined. The aqueous solution was then concentrated (aspirator) to a smaller volume (ca. 250 mL) and allowed to cool to ambient temperature overnight. The resulting crystalline solid was removed by filtration, washed with a small portion of water followed by ethanol, and dried as above to give 11.0 of product with the same purity (by tlc) as that of first crop. In a similar manner the mother liquor from the first crop was treated as described above to give 10.5 g of product of the same purity (tlc) as the other crops. The combined yield was 100 g (70% calculated as the monohydrate).

In this manner, 785 g of well-dried (24 h, 90° C., 0.3 mmHg), essentially anhydrous starting nucleoside (VII) was processed to give 799 g (76%, calculated as a monohydrate) of good quality target compound (VIII). However, in the initial series of runs, 510 g of nucleoside as the monohydrate was processed to give but 351 g (54%). This corresponds to an overall yield of 1150 g (68%) from 1295 g of precursor (VII) (See Note 1).

Final Recrystallization (See Note 2)

The above material, 1134 g, in five batches was dissolved in preheated deionized water (82° C., 15 mL/g). The compound dissolved in 3-5 minutes at 73°-75° C. The solutions from the five batches was filtered through paper and the filtrate was transferred to a 22 L flask. The solution was stirred and cooled rapidly to 45°-50° C. to minimize product decomposition. At this point, the product started to crystallize and the mixture was allowed to cool slowly over about one hour until the precipitation was essentially complete (see Note 3). The solution was then cooled (water-bath) over 2 hours to 22° C. and then cooled (ice-bath) for one hour. The resulting precipitate (a milky slurry) was collected by filtration through filter-cloth in four batches which requires 6 hours to complete. The filter cake was washed successively with cold deionized water (1.25 L) and ethanol (1.8 L).

The product was dried at room temperature at 0.3 mmHg for 24 hours and weighed 916 g as a 0.8 hydrate at this point. The product was dried further at 55°-60° C. at 0.3 mmHg for 72 hours to give 881 g (82% recovery) of anhydrous material. The average yield was 56% from the precursor nucleoside VII. The mother liquor can be reworked and additional product isolated.

Note 1: In exploratory work the nucleoside (VII), after air-drying was dried under vacuum at room temperature for several days to yield a monohydrate. The monohydrate dissolved readily (~20 min) in the reaction medium as the reaction proceeded, the excess phosphorus oxychloride appeared adequate to destroy the water of hydration and the yields were 65-68%. In the current work the 10 g probe run and two of the next three 100 g runs gave acceptable yields. However, in the last two 100 g runs (ran simultaneously) the yields averaged 41% and trial runs were reinstituted to correct the problem.

First the nucleoside was dried 24 hours at 0.33 mmHg and 90° C. to give essentially anhydrous material. The trimethylphosphate reaction solvent was distilled and the forerun and tail fractions were discarded. With these changes the time to obtain a homogeneous reaction system was extended to 2 hours and 50 minutes, but the yields were both reproducible and markedly improved (75-79%, average 76%) based on product (VIII) as a monohydrate after drying at room temperature for 4 hours at 0.3 mmHg.

Note 2: In view of the extensive handling in the last step, a final recrystallization was necessary to remove any inadvertently-introduced water-insoluble impurities. The acidic product is, however, unstable in hot water. Some decomposition occurs during the recrystallization and no real improvement in purity results. With careful handling in the last step, it is possible that the final recrystallization can be avoided.

Note 3: If the temperature is allowed to fall to 32°-33° C. before precipitation is complete, the product will precipitate as a gel.

Materials trimethylphosphate
Phosphorous oxychloride (d=1.645)
Methylene chloride
Molecular sieves, 4A
Dowex 50W-X2, 50-100 mesh
Alcohol, 3A, specially denatured

PHYSICAL AND ANALYTICAL DATA

2-Fluoro-ara-adenosine 5'-phosphate, NSC 312887

Lot No. 3

Melting Point: 202°-203° C. (dec), browns at 190° C.
Analysis: Calcd for $C_{10}H_{13}FN_5O_7P$ (365.21):

|   | Calcd | Found |
|---|-------|-------|
| C | 32.89 | 32.77 |
| H | 3.59  | 3.74  |
| N | 19.17 | 19.04 |
| F | 5.20  | 4.96  |
| P | 8.48  | 8.40  |

Ultraviolet Spectral Data: (pH 7 Buffer) lambda max ($H_2O$) 262 nm $\epsilon$14,900; (0.1N HCl) lambda max ($H_2O$) 262 nm $\epsilon$13,100; (0.1N NaOH) lambda max ($H_2O$) 261 nm $\epsilon$15,600.

Thin Layer Chromatograph: (EM Silica gel 60F-254, 240) iso-PrOH—$H_2O$—$NH_4OH$ (7:2:1), $R_f$=0.30, trace impurity; n-PrOH—MeOH—$H_2O$—$NH_4OH$ (4:3:2:1), $R_f$=0.41, impurity. MeOH-$H_2O$-$NH_4OH$ (75:25:1), $R_f$=0.70, trace impurity:

Solubility Data: 25° C., without heating (Ref 1). Free Acid: Water: 9 mg/mL (8.7 and 9.3 mg/mL), 2 det'ns, pH~2. Ethanol: Insoluble. Sodium salt: Water: >100 mg/mL (upper limit not determined).

Comparative Example 2

Compound (VI) (3.6 mmole) and palladium chloride (1.4 g, 7.9 mmole) were used as in Example 1. The pressure was about 35 psig. The reaction was complete in about 1 hour and gave a 66% yield of product (VII). The amount of catalyst was 70% by weight or 2.2 moles per mole of (VI). The yield was not optimal and there was a risk of defluorination of (VI). Too much catalyst was necessary.

Example 3

The reaction conditions of Example 2 were modified by the addition of hydrochloric acid. Thus compound (VI) (10 g, 18 mmol) $PdCl_2$ (1.5 g, 8.5 mmol) and hydrochloric acid 5 mL, 60 mmol was hydrogenated to give compound (VI)I in 70% yield. The yield was raised in subsequent hydrogenations using 50 g of compound (VI) to 80% or better. The amount of palladium chloride used was only 15% by weight of compound (VI) and the reaction was completed in 25-30 minutes.

Example 4

In a further modification of Example 3, charcoal (Norit A TM) was added to the hydrogenation mixture. This allowed a further reduction in the amount of palladium chloride used to 3% by weight of compound (VI) without reducing the product yield or affecting the reaction time. The pH of hydrochloric acid in methoxyethanol in Examples 3 and 4 was measured and it was less than pH 0.

Thus, by this process of the present invention, highly active palladium catalyst is generated from palladium chloride and hydrochloric acid which leads to the rapid cleavage of the benzyl protecting groups without defluorination of the purine ring.

It is intended that the foregoing description be only illustrative of the present invention and that the present invention be limited only by the hereinafter appended claims.

I claim:

1. A process for the preparation of 9-beta-D-arabinofuranosyl-2-fluoroadenine (VII) which consists essentially of:
   (a) reacting a mixture of 2-fluoro-9-(2,3,5-tri-O-benzyl-beta-D-arabinofuranosyl)adenine (VI) dissolved in a non-reactive solvent for (VI), with hydrogen and a molar amount of palladium chloride less than (VI) and concentrated hydrochloric acid in a molar excess to (VI) such that the weight of palladium chloride is between about 3 and 15% by weight of (VI) in a sealed vessel at elevated pressure above atmospheric pressure between about 30 and 50 psig to produce (VII) in the reaction mixture;
   (b) removing the palladium chloride from the reaction mixture;
   (c) neutralizing the reaction mixture; and
   (d) separating 2-fluoro-9-beta-D-arabinofuranosyl adenine from the reaction mixture.

2. The process of claim 1 wherein the solvent is methoxyethanol.

3. The process of claim 1 wherein the reaction is started at about 17° C. and ends at about 38° C.

4. The process of claim 1 wherein the hydrochloric acid is present in a molar ratio above about 3 times the moles of (VI).

5. The process of claim 1 wherein the pressure is about 35 psig.

6. The process of claim 1 wherein charcoal is provided in the reaction mixture.

* * * * *

UNITED STATES PATENT AND TRADEMARK OFFICE
CERTIFICATE OF CORRECTION

PATENT NO. : 5,296,589

DATED : March 22, 1994

INVENTOR(S) : Peter Blumbergs

It is certified that error appears in the above-indentified patent and that said Letters Patent is hereby corrected as shown below:

Column 1, line 10, "No. 5,118,919", should read --5,110,919--.

Column 2, line 40, the structure " 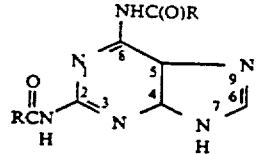 "

should read -- 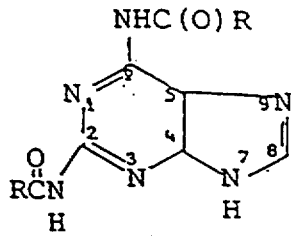 --.

Column 4, line 62, "the" should be --The--.

UNITED STATES PATENT AND TRADEMARK OFFICE
CERTIFICATE OF CORRECTION

PATENT NO. : 5,296,589
DATED : March 22, 1994
INVENTOR(S) : Peter Blumbergs

It is certified that error appears in the above-indentified patent and that said Letters Patent is hereby corrected as shown below:

Column 6, line 55, "155°-7°C." should read --155°-157°C.--.

Column 7, line 15, "156°-58°C." should read --156°-158°C.--.

Column 7, line 28, "-beat-" should read -- -beta- --.

Column 7, line 61, "(-55 mL)" should read --(~55mL)--.

Column 8, line 12, "2.42" should read --4.24--.

Column 8, line 36, "(-1°C)" should read --(~1°C)--.

Column 8, line 44, "(-50°C)" should read --(~50°C)--.

Column 8, line 65, "11.0" should read --11.0g--.

Column 10, line 35, before "impurity", --trace-- should be inserted.

Signed and Sealed this

Thirtieth Day of August, 1994

Attest:

*Attesting Officer*

BRUCE LEHMAN

*Commissioner of Patents and Trademarks*